United States Patent [19]

Piccolo et al.

[11] Patent Number: 4,736,061

[45] Date of Patent: Apr. 5, 1988

[54] PROCESS FOR PREPARING NAPROXEN

[75] Inventors: Oreste Piccolo, Livorno; Ermanno Valoti, Dalmine; Giuseppina Visentin, Monza, all of Italy

[73] Assignee: Blaschim S.p.A., Milano, Italy

[21] Appl. No.: 732,735

[22] Filed: May 10, 1985

[30] Foreign Application Priority Data

May 10, 1984 [IT] Italy .................. 20859 A/84

[51] Int. Cl.$^4$ .................. C07C 59/64; C07C 67/36; C07C 49/782
[52] U.S. Cl. .................. 562/466; 560/56; 568/315; 568/328
[58] Field of Search .................. 562/466

[56] References Cited

U.S. PATENT DOCUMENTS

| | | | |
|---|---|---|---|
| 3,884,950 | 5/1975 | Koda et al. | 556/401 |
| 4,107,439 | 8/1978 | Walker et al. | 562/466 X |
| 4,423,244 | 12/1983 | Cannata et al. | 562/466 |
| 4,510,321 | 4/1985 | Masilamani et al. | 562/421 |
| 4,582,930 | 4/1986 | Castaldi et al. | 562/466 X |

FOREIGN PATENT DOCUMENTS

| | | |
|---|---|---|
| 34871 | 9/1981 | European Pat. Off. . |
| 67698 | 12/1982 | European Pat. Off. . |
| 81993 | 6/1983 | European Pat. Off. . |

OTHER PUBLICATIONS

Desai, A. P. et al., 3. Indian Chem. Soc., vol. 47, No. 2, pp. 117–118, 1970.

*Primary Examiner*—Donald B. Moyer
*Assistant Examiner*—Patricia M. Scott
*Attorney, Agent, or Firm*—Berman, Aisenberg & Platt

[57] ABSTRACT

Process for preparing Naproxen via a sequence of stereospecific reactions which comprises: condensation of 1-chloro-2-methoxy-naphthalene with a (S)-2-halo-propionyl halide according to the Friedel-Crafts reaction, ketalization of the thus obtained (S)-2-halo-1-(5'-chloro-6'-methoxy-2'-naphthyl)-propan-1-one, rearrangement of said ketal to afford an ester, hydrolysis of the ester and removal of the chlorine atom in 5-position by hydrogenolysis.

New (S) 2-halo-1-(5'-chloro-6'-methoxy-2'-naphthyl)-propan-1-ones.

7 Claims, No Drawings

PROCESS FOR PREPARING NAPROXEN

This invention relates to a process for the preparation of Naproxen via a sequence of stereospecific reactions which comprises: condensation of 1-chloro-2-methoxy-naphthalene with a (S)-2-halo-propionyl halide according to the Fridel-Crafts reaction, ketalization of the thus obtained (S)-2-halo-1-(5'-chloro-6'-methoxy-2'-naphthyl)-propan-1-one, rearrangement of said ketal to afford an ester, hydrolysis of the ester and removal of the chorine atom in 5-position by hydrogenolysis. In said sequence hydrogenolysis of the chlorine atom can precede hydrolysis of the ester.

Naproxen (Merck Index, IX ed., page 834) is a known drug endowed with antiinflammatory, analgesic and antipyretic activity.

Of the two possible enantiomers only the (S) enantiomer is used for therapeutic purposes. The majority of known synthetic routes call for the preparation of the racemate, separation of the (S) enantiomer, racemization of the (R) enantiomer, further separation of the (S) enantiomer and so on.

These steps greatly increase the production costs of Naproxen.

A need is therefore very strongly felt for a stereospecific synthesis which would avoid the inconvenience mentioned above.

European Patent application No. 82303068.9 describes a process which would provide for the preparation of optically active arylalkanones by the Friedel-Crafts reaction according to the following diagram:

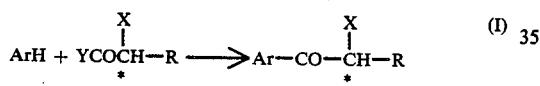

where Ar is an aromatic group, R is an aliphatic group, X is a halogen or a sulfonyloxy group and Y is a halogen.

In the aforementioned European Patent Application it is maintained that the very well-known Friedel-Crafts reaction is suitable for preparing all the innumerable optically active arylakanones embraced by formula I without any exceptions and it is also maintained that this is unexpected.

European Patent application No. 82306603.0 describes the preparation of said optically active arylalkanones of formula I with the equally well-known Grignard reaction. Here again there is the assertion that the result is unexpected.

According to both said European patent applications subsequent treatment of optically active arylalkanones to give the corresponding optically active arylalkanoic acids can follow the route described in European Patent Application No. 81200210.3.

Even though European Patent application No. 82303068.9 indicates Naproxen as one of the optically active arylalkanoic acids which can be prepared with the process described therein, in reality said patent application does not give any examples thereof.

European patent application No. 82306603.0 gives several examples of stereoselective synthesis of Naproxen but this method suffers from the difficulty, well-known to the artisan, in performing the Grignard reaction on an industrial scale, and calls for the use of 2-bromo-6-methoxy-naphthalene, the synthesis of which is considerably more complex than that of 1-halo-2-methoxy-naphthalenes.

In 1970 A. P. Desai et al (3. Indian Chem. Soc., Vol. 47, No. 2, pages 117-8; 1970) had found that optically active arylalkanones can be prepared according to both the Friedel-Crafts and the Grignard reaction from an aromatic compound and an optically active derivative of an alkanoic acid. In other words, the conditions under which the Friedel-Crafts and the Grignard reaction are performed may not cause racemization of the optically active alkanoic acid derivative which is used.

In view of the above mentioned teachings it might seem easy to prepare Naproxen through the optically active compounds of the formula

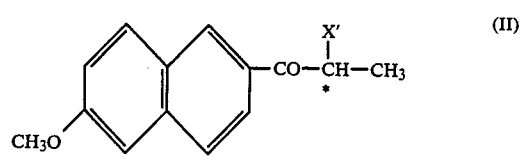

where X' is Cl or Br, obtained with the Friedel-Crafts reaction.

Surprisingly, however, several attempts (see examples 4 and 5 below) made to prepare compounds II by the Friedel-Crafts reaction according to the following diagram:

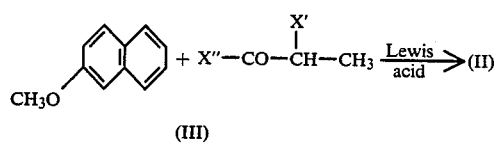

where X' and X'', the same or different, are chlorine or bromine; did not yield compounds II and this is surprising considering that the halide of the propionic acid affords the desired product with practically quantitative yields according to the following diagram:

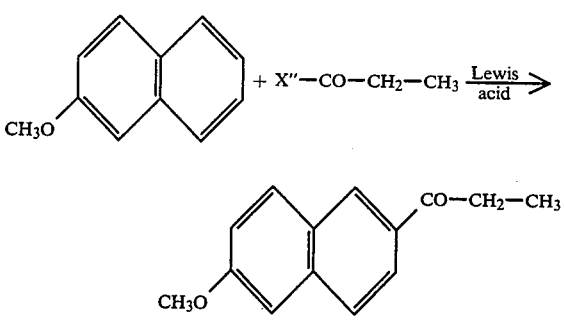

It has now been found that the compounds of formula

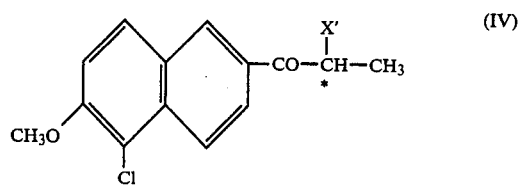

where X' has the above meanings, can be prepared in optically active form with high yields according to the Friedel-Crafts reaction and that they are particularly useful as intermediates in the stereospecific synthesis of Naproxen.

And this is all the more surprising considering that when the Friedel-Crafts reaction is carried out by reacting a compound of formula III with 1-bromo-2-methoxy-naphthalene (see example 3, below) only small quantities are obtained of the bromine derivative analogous of the compound of formula IV, together with various other compounds from which the compound of formula IV can be separated only with much difficulty.

The object of the present invention is hence a stereospecific preparation process for Naproxen which comprises the preparation, in accordance with the Friedel-Crafts reaction, of an optically active compound of formula IV.

Another object of the present invention consists of the new optically active compounds of formula IV.

Other objects and advantages of the present invention will become apparent from the following detailed description and from the examples.

The stereospecific preparation for Naproxen according to the present invention is accomplished in the following steps:

(a) reaction of the 1-chloro-2-methoxy-naphthalene with an optically active compound of formula III to give an optically active compound of formula IV having absolute configuration (S);

(b) ketalization of the compound of formula IV under nonracemizing conditions with an alcohol having from 1 to 12 carbon atoms to give an optically active ketal having absolute configuration (S);

(c) rearrangement of the ketal into an optically active ester having absolute configuration (S).

(d) hydrolysis of this last under nonracemizing conditions;

(e) removal by means of hydrogenolysis under nonracemizing conditions of the chlorine atom in 5-position.

The sequence given above is not binding since step (e) can precede step (d).

Step (a) is carried out in the presence of a suitable catalyst, such as aluminum chloride, preferably in the presence of a suitable solvent and at a temperature from 10° C. to 35° C.

Step (b) is preferably carried out with a lower aliphatic alcohol, such as methanol in the presence of the corresponding orthoformate and using an excess of alcohol or orthoformate, which also act as solvents. To this mixture can also be added another solvent which promotes even more dissolving of the substrate. Suitable solvents are aromatic hydrocarbon such as benzene and toluene. Preferred reaction temperature is that of reflux of the reaction mixture.

Step (c) is preferably carried out in the presence of a suitable catalyst. Examples of suitable catalysts are inorganic derivatives of zinc, such as zinc chloride, bromide and oxide.

Concerning step (d) it was seen that in basic conditions the racemization speed of the ester is greater than hydrolysis speed. It is therefore preferred to operate under acid conditions, however avoiding agents, such as hydrobromic acid, or conditions which cause partial or total demethylation of the methoxy group. Suitable conditions are those obtained using hydrochloric acid and a suitable solvent, such as acetone, at temperatures below 60° C. Similarly, the reaction can be performed with formic acid or acetic acid in the presence of catalytic amounts of a mineral acid at temperatures below 60° C.

When the hydrogenolysis (step e) is performed on the acid compound, it can be carried out under basic, neutral or acid conditions using hydrogen or a hydrogen transferrer in the presence of appropriate catalysts and suitable solvents on condition, however, of not using alcohols (when operating under acid conditions) to avoid the formation of the corresponding ester. When the hydrogenolysis is performed on the ester compound, i.e. before step (d), care must be taken to avoid basic conditions to prevent racemization of the ester. In general care must be taken to perform the hydrogenolysis under the mildest conditions compatible with the system used.

The expression "nonracemizing conditions" is used in this description to indicate that racemization is reduced to a minimum and that the formation of enantiomer R usually does not exceed five percent.

The following examples illustrate the invention without limiting it in any way.

EXAMPLE 1

To a mixture of 7.3 g (54.7 mmol) of $AlCl_3$ in 25 ml of methylene chloride kept at 20°–25° C. are gradually added 7.2 g (56.7 mmol) of (S)-2-chloro-propionyl-chloride $[\alpha]_D^{25}+5.44°$ (pure liquid; l=1 dm) and 7.0 g (36.4 mmol) of 1-chloro-2-methoxy-naphthalene. After further 4 hrs at 20°–25° C., the mixture is hydrolized and worked up according usual procedures to give 10.2 g of a crude product which after recrystallization from a mixture heptane/methanol (3/2, v/v) affords 6.2 g (yield, 60%) of (S) 2-chloro-1-(5'-chloro-6'-methoxy-2'-naphthyl)-propan-1-one melting at 123° C., $[\alpha]_D^{25}+108.5$ (C=0.8; $CHCl_3$). NMR ($CDCl_3$, TMS as reference): 1.5 (3H, d, $CHCH_3$), 3.7 (3H, s, $OCH_3$), 5.0 (1H, q, CH), 8.0–6.5 (5H, m, aromatic hydrogens), mass (m/e): 282–284 (M+, 21%), 219–21 (100%).

EXAMPLE 2

Repeating the procedure of Example 1 but replacing (S)-2-bromo-propionyl chloride for (S)-2-chloro-propionyl chloride are obtained 10.5 g (yield, 89%) of (S)-2-bromo-1-(5'-chloro-6'-methoxy-2'-naphthyl)-propan-1-one.

EXAMPLE 3

Repeating the procedure of Example 1, but replacing 1-chloro-2-methoxy-naphthalene by 1-bromo-2-methoxy-naphthalene yields 1.7 g (yield, 15%) of (S)-2-chloro-1-(5'-bromo-6'-methoxy-2'-naphthyl)-propan-1-one.

EXAMPLE 4

Repeating the procedure of Example 1, but replacing 1-chloro-2-methoxy-naphthalene by 2-methoxy-naphthalene yields a crude product consisting mainly of (S) 2-chloro-1-(2'-methoxy-1'-naphthyl)-propan-1-one wherein the ratio between this compound and the corresponding (6'-methoxy-2'-naphthyl) isomer is about 93/7 (HPLC analysis).

EXAMPLE 5

Repeating the procedure of Example 2, but replacing 1-chloro-2-methoxy-naphthalene by 2-methoxy-naphthalene yields a crude product consisting mainly of (S)

2-bromo-1-(2'-methoxy-1'-naphthyl)-propan-1-one wherein the ratio between this compound and the corresponding (6'-methoxy-2'-naphthyl) isomer is about 70/30.

EXAMPLE 6

A mixture of 6.2 g (21.9 mmol) of (S)-2-chloro-1-(5'-chlor-6'-methoxy-2'-naphthyl)-propan-1-one, obtained according to Example 1, 60 ml of methanol, 13 ml of toluene, 14.5 g (135.8 mmol) of trimethylorthoformate and of 1.2 g of 96% sulfuric acid is refluxed for 23 hours while distilling about 25% of the solvent. When the reaction is over, the mixture is neutralized with an aqueous solution of sodium carbonate. The toluene layer is separated and concentrated to give 7.0 g of (S)-2-chloro-1,1-dimethoxy-1-(5'-chloro-6'-methoxy-2'-naphthyl)-propane; a sample is purified by cromatography on silica gel (eluents: petroleum ether/ethyl acetate 90/10), m.p. 106° C., $[\alpha]_D^{25}+25.0$ (C=1.0; CHCl$_3$).

EXAMPLE 7

A mixture of 6.0 g (18.2 mmol) of (S)-2-chloro-1,1-dimethoxy-1-(5'-chloro-6'-methoxy-2'-naphthyl)-propane, obtained according to Example 6, 55 mg (0.4 mmol) of zinc chloride and of 120 ml of toluene is refluxed while distilling the solvent until the internal temperature is of about 120° C. After 3 hours the reaction mixture is treated with animal charcoal, filtered and concentrated to afford 5.1 g of methyl (S)-2-(5'-chloro-6'-methoxy-2'-naphthyl)-propionate; a sample is purified by chromatography on silica gel (eluents: heptane/ethyl acetate 95/5), m.p. 102° C., $[\alpha]_D^{25}+60.78$ (C=1.0; CHCl$_3$).

Similar results are obtained replacing zinc bromide for zinc chloride.

EXAMPLE 8

Repeating the procedure of Example 7, but replacing zinc chloride by zinc oxide as catalyst yields 5.1 g of methyl (S)-2-(5'-chloro-6'-methoxy-2'-naphthyl)-propionate, $[\alpha]_D^{25}+62.87$ (C=1.0; CHCl$_3$) after crystallization from heptane.

EXAMPLE 9

A mixture of 3.0 g (10.8 mmols) of methyl (S) 2-(5'-chloro-6'-methoxy-2'-naphthyl)-propionate, obtained according to the procedure of Examples 7, of 20 ml of 37% HCl and of 20 ml of acetone is refluxed for 3 hours. After usual treatments 2.6 g of (S) 2-(5'-chloro-6'-methoxy-2'-naphthyl)-propionic acid, m.p. 158° C., $[\alpha]_D^{25}+48.59$ (C=1.0; CHCl$_3$), are obtained

EXAMPLE 10

A mixture of 0.94 g (3.6 mmol) of (S)-2-(5'-chloro-6'-methoxy-2'-naphthyl)-propionic acid, obtained according to Example 9, of 0.8 ml (8.0 mmol) of 30% sodium hydroxide and of 90 mg of Raney Nickel in 7 ml of water, is admixed slowly at 75° C. with 1 ml (25.0 mmol) of 80% hydrazine hydrate. After 3 hrs the mixture is filtered and made acid up to pH 1 to give 0.7 g of (S)-2-(6'-methoxy-2'-naphthyl)-propionic acid, $[\alpha]_D^{25}+64.36$ (C=1.0; CHCl$_3$).

EXAMPLE 11

A mixture of 3.0 g (10.8 mmol) of ethyl (S)-2-(5'-chloro-6'-methoxy-2'-naphthyl)-propionate, obtained according to Example 8, and of 0.3 g of 10% Pd/C in 20 ml of methanol is hydrogenated at atmospheric pressure and at room temperature to give 2.4 g of methyl (S)-(6'-methoxy-2'-naphthyl)-propionate, $[\alpha]_D^{25}+72.4$ (C=1.0; CHCl$_3$).

EXAMPLE 12

2.0 g (8.2 mmol) of methyl (S)-2-(6'-methoxy-2'-naphthyl)-propionate, obtained according to Example 11, are hydrolized according to the procedure of Example 9 to give 1.8 g of (S)-2-(6'-methoxy-2'-naphthyl)-propionic acid, $[\alpha]_D^{25}+63.40$ (C=1.0; CHCl$_3$).

We claim:

1. In a process for preparing naproxen via reaction of a naphthalene starting compound with an optically-active compound of the formula

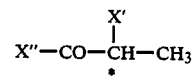

(where each of X' and X" is, independently, chlorine or bromine) according to the Friedel-Crafts reaction, ketalization of the thus-obtained (S) 2-halo-1-(5'-chloro-6'-methoxy-2'-naphthyl)-propan-1-one with a lower aliphatic alcohol in the presence of the corresponding orthoformate, rearrangement of the resulting ketal compound in the presence of an inorganic zinc catalyst to obtain an alkyl (S) 2-(5'-chloro-6'-methoxy-2'-naphthyl)-propionate, hydrolyzation of the thus-obtained ester compound under acid conditions to obtain the (S) 2-(5'-chloro-6'-methoxy-2'-naphthyl)-propionic acid, and hydrogenolysis of the resulting acid compound, the improvement wherein the naphthalene starting compound is 1-chloro-2-methoxy-naphthalene.

2. A process according to claim 1, wherein ketalization is effected with methanol and methyl orthoformate.

3. A process according to claim 1 above, wherein the zinc catalyst is zinc chloride, bromide or oxide.

4. A process according to claim 1 above, wherein the hydrolyzation is performed with hydrochloric, formic or acetic acid at a temperature below 60° C.

5. In a process for preparing Naproxen via reaction of a naphthalene starting compound with an optically-active compound of the formula

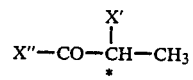

(where each of X' and X" is, independently, chlorine or bromine) according to the Friedel-Crafts reaction, ketalization of the thus-obtained (S) 2-halo-1-(5'-chloro-6'-methoxy-2'-naphthyl)-propan-1-one with a lower aliphatic alcohol in the presence of the corresponding orthoformate, rearrangement of the resulting ketal compound in the presence of an inorganic zinc catalyst to obtain an alkyl (S) 2-(5'-chloro-6'-methoxy-2'-naphthyl propionate, hydrogenolysis of the thus-obtained ester compound, and hydrolyzation of the thus-obtained product under acid conditions, the improvement wherein the naphthalene starting compound is 1-chloro-2-methoxy-naphthalene.

6. A process according to claim 5, wherein the hydrogenolysis is performed under neutral or acid conditions.

7. A process for preparing Naproxen, which comprises:

(a) ketalizing an optically-active arylalkanone hving (S) absolute configuration and of the formula:

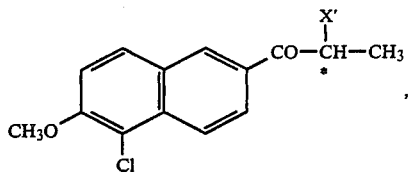

(IV)

wherein X' is chlorine or bromine, with a lower aliphatic alcohol in the presence of the corresponding orthoformate, (b) rearranging the obtained ketal compound in the presence of an inorganic zinc catalyst to obtain an alkyl (S) 2-(5'-chloro-6'-methoxy-2'-naphthyl)-propionate, (c) hydrolyzing the thus-obtained ester compound under acid conditions to obtain the (S) 2-(5'-chloro-6'-methoxy-2'-naphthyl)-propionic acid, and (d) subjecting the resulting acid compound to hydrogenolysis.

* * * * *